United States Patent [19]

Ito et al.

[11] Patent Number: 4,715,719
[45] Date of Patent: Dec. 29, 1987

[54] METHOD OF PREPARING MORTAR OR CONCRETE

[75] Inventors: Yasuro Ito; Yoshiro Higuchi, both of Tokyo; Takeshi Shiki, Funabashi; Yukikazu Tsuji, Ashikaga; Masanori Tsuji, Osaka; Mitsutaka Hayakawa, Kamakura, all of Japan

[73] Assignee: Yasuro Ito and Taisei Corporation, Tokyo, Japan

[21] Appl. No.: 882,034

[22] PCT Filed: Jan. 18, 1984

[86] PCT No.: PCT/JP84/00008

§ 371 Date: Sep. 13, 1984

§ 102(e) Date: Sep. 13, 1984

[87] PCT Pub. No.: WO84/02872

PCT Pub. Date: Aug. 2, 1984

Related U.S. Application Data

[63] Continuation of Ser. No. 654,003, Sep. 13, 1984, abandoned.

[30] Foreign Application Priority Data

Jan. 18, 1983 [JP] Japan .................................. 58-5216
Apr. 5, 1983 [JP] Japan ................................ 58-58639

[51] Int. Cl.[4] .............................................. B28C 5/00
[52] U.S. Cl. .................................................... 366/2
[58] Field of Search ...................... 366/1, 2, 6, 8, 16, 366/40, 17, 18

[56] References Cited

U.S. PATENT DOCUMENTS

| | | | |
|---|---|---|---|
| 2,167,156 | 7/1939 | Morrissey | 366/8 |
| 3,230,589 | 1/1966 | McIlvaine | 366/8 |
| 3,669,418 | 6/1972 | Cornwell | 366/5 |
| 4,335,966 | 6/1982 | Rapp | 366/2 |

Primary Examiner—Robert W. Jenkins
Attorney, Agent, or Firm—Birch, Stewart, Kolasch and Birch

[57] ABSTRACT

A method and apparatus of measuring water percentages of a fine aggregate comprising the steps of prewetting the fine aggregate, containing the prewetted fine aggregate in an air-tightly closed container, applying a centrifugal force to said container over a predetermined period to remove a portion of a quantity of water deposited on the fine aggregate, and measuring the water content remaining in or on the fine aggregate after being subjected to the centrifugal force, and thus determining a percentage of water adhered to the fine aggregate and a percentage of water of the fine aggregate in which interstice thereof is saturated with water while a surface thereof is dry.

5 Claims, 16 Drawing Figures

FIG. 2
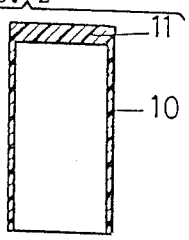
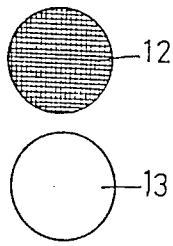
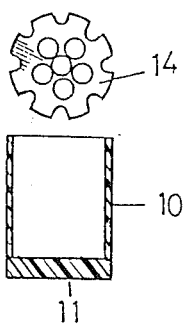
FIG. 3
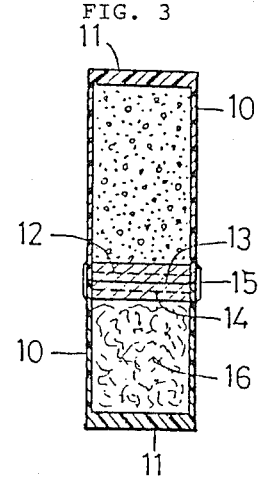
FIG. 4
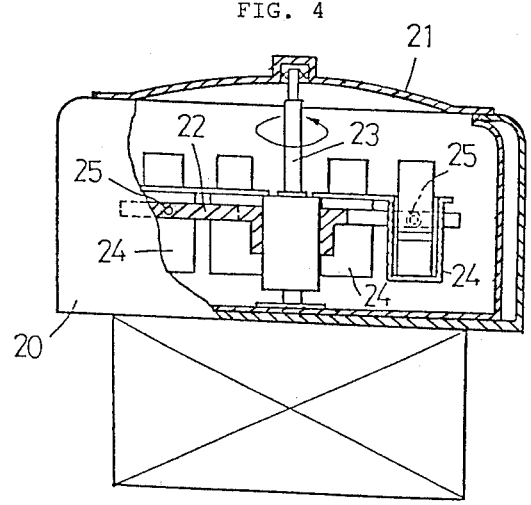

CENTRIFUGAL FORCE APPLYING PERIOD (min.)

METHOD OF PREPARING MORTAR OR CONCRETE

This application is a continuation of application Ser. No. 654,003, filed on Sept. 13, 1984, now abandoned.

FIELD OF THE INVENTION

This invention relates to a method of preparing mortar or concrete, more particularly to a method of measuring and adjusting a quantity and state of water adhered to the surface of a fine aggregate used to prepare mortar or concrete by admixing with a powder of hydraulic compound such as cement and plaster and water (and a coarse aggregate), and further to a method and device for measuring water content in a fine aggregate used for preparation of mortar or concrete.

BACKGROUND OF THE INVENTION

It has been widely practiced to prepare a mortar by admixing together a powder of hydraulic compound such as cement and plaster, water and a fine aggregate such as sand and also to prepare a concrete by utilizing a coarse aggregate such as gravel as well as these ingredients. However, a fresh or liquid concrete or mortar prepared by the conventional method can not manifest uniform property or characteristics (e.g., segregation, bleeding, fluidability). More particularly, even when the same kind of hydraulic compound and fine aggregate are used in the same quantities and the same quantity of water is added in the same manner to a mixture of the hydraulic compound and fine aggregate, the characteristics of the resulting fresh mixture will be greatly varied in each case, which would be caused by the fact that a quantity and state of water adhered to the surface of the fine aggregate thus used be respectively varied.

Consequently, in the preparation of mortar or concrete it is essential to determine the quantity and state of the surface water of the fine aggregate. For this purpose it has been considered that the quantity and state of the surface water of the aggregate should be measured in accordance with JIS (Japanese Industrial Standards) A1109 entitled "Method of Test for Specific Gravity and Water Absorption of Fine Aggregate". According to this method, by poking operation with a stick (340±15 g weight, 25±5 mm diameter) a test sample of fine aggregate is filled up into a metallic flow corn having inner diameters of 38 mm at the top and 89 mm at the bottom respectively and 74 mm height, and the flow corn thus filled with the fine aggregate is placed on a horizontal base and then drawn up. The fine aggregate is defined as being in an interstice-water saturated and surface-dry condition, when the corn-shaped accumulation of fine aggregate is firstly destroyed or slumped down. It is a conventional thought that in this condition the interstice of fine aggregate is saturated with water while the surface is substantially dry and that the water content of the fine aggregate in this condition determined by the method of JIS A1109 does not influence the characteristics of the resulting mortar or concrete and therefore can be disregarded in determination of total quantity of water necessary to prepare mortar or concrete. Thus, where the percentage of water contained in or adhered to the fine aggregate which must be taken into consideration in determination of the water quantity necessary for preparing mortar or concrete is hereby defined as "effective water percentage" and in turn the percentage of water which may be excluded from the necessary water quantity is defined as "ineffective water percentage", it has been recognized that the water percentage of the fine aggregate in a saturated surface-dry condition as determined by JIS A1109 (hereinafter called "JIS surface-dry water percentage") will be equal to the ineffective water percentage. However, as a result of our careful investigation it has been found that such a conventional recognition is not correct so that if mortar or concrete prepared according to the conventional recognition could not provide uniform characteristics.

Meanwhile, we have already proposed an epoch-making process of preparing mortar or concrete which is disclosed in Japanese Laid Open Patent No. 104958/1980 and U.S. Pat. No. 4,299,633 wherein the necessary water quantity is divided into two portions, namely primary water is incorporated with fine aggregate and cement followed by first kneading operation and then secondary water (and additives, if necessary) is added to the resulting mixture followed by second kneading operation. It has been confirmed that this method is capable of manufacturing mortar or concrete with a sufficient mechanical strength and constant properties. In order to achieve such advantageous results, however, this method will require that a water quantity adhered to the fine aggregate itself be accurately determined and adjusted to a certain value, which has been difficult according to the prior art method described before.

Accordingly an object of the invention is to clarify the influence of the quantity and/or percentage of water adhered to a fine aggregate to be used in preparation of mortar or concrete upon characteristics of a resulting mortar or concrete, and thereby providing a method of preparing mortar or concrete having improved and uniform characteristics.

Another object of the invention is to provide a novel method and device capable of definitely measuring a percentage of water adhered to a fine aggregate to be used in preparation of mortar or concrete.

DISCLOSURE OF THE INVENTION

With respect to various sand samples collected in the Ohoi River and having different JIS surface-dry water percentages, that is a sample C (JIS surface-dry percentage of 2.8%), a sample E (JIS surface-dry water percentage of 1.3%) and a crushed sand (JIS surface-dry water percentage of 2.3%), they were treated with a vacuum mixer with a reduced pressure of 730 mmHg so as to prevent air voids or films from remaining on the surface thereof and adjusted to have predetermined percentages of water content by adding thereto a quantity of water under the pressure reduced condition. Then, these samples were charged into a container of acrylic resin and compacted with 15 times up-and-down operation of the container. The weight of the compacted mass of was measured, followed by a measurement of the percentage of water content and the percentage of bulking (based on an absolutely dry condition) thereof, the results of which are shown in FIG. 1.

FIG. 1 shows that the percentage of bulking varies with the percentage of water content of the aggregate even if the aggregate contains water in a percentage smaller than the JIS surface-dry water percentage, and the variation of bulking percentage of the aggregate having a percentage of water smaller than the JIS surface-dry water percentage is rather significant than that in the case of a water percentage being larger than the JIS surface-dry water percentage. This would mean that a minimum quantity or percentage ($\beta$lim) of water will be still adhered to the surface of the aggregate in the JIS surface dry condition, and the variation of the water percentage in a region of $0 - \beta$lim will result in a variation of the bulking. More particularly, the JIS surface-dry water percentage Q is not equal to the water percentage $Q_0$ of the aggregate wherein interstice thereof is saturated with water while the surface is dry, as having been recognized, but should be expressed by the equation : $Q = Q_0 + \beta$lim. Thus, it has been confirmed that the ineffective water is in fact to correspond to only $Q_0$.

The JIS surface-dry water percentage Q can be determined according to the method of JIS A1109 which will, however, involve the step of immersing the fine aggregate in water for 24 hours. We have also studied a method for readily determining the JIS surface-dry water percentage Q and succeeded to find out a novel method according to which a value Q' corresponding to Q can be determined in a relatively short time (i.e., less than 10 min.), in which method two types of fine aggregate are used, one is prepared by adding a quantity of water to the fine aggregate in an absolutely dry state under a pressure reduced condition followed by first kneading, by returning the pressure to the atmosphere and by again reducing the pressure followed by second kneading and the other is prepared by adding a quantity of water to the fine aggregate in an absolutely dry state under an atmospheric pressure condition followed by kneading in a given period. Although the value Q' obtained by the above method is not exactly equal to the JIS surface-dry water percentage Q, it is a reliable value and would be rather reliable than Q which could be varied by a possible difference or error in various condition or operation involved in the JIS method, for example incorporation of water, drying, charging operation with a stick, discrimination of the slump of a corn-shaped accumulation of fine aggregate, etc.

As described above, it is herein proposed to determine and use a number of values as standards of percentage of water contained in or adhered to the fine aggregate, not only the JIS surface-dry water percentage Q which has been considered to be the one and only standard, but also another water percentage $Q_0$ of the aggregate wherein the interstice thereof is saturated with water while the surface is dry (which value is a real surface-dry water percentage) and the minimum adhesion water percentage $\beta$lim. Moreover, it has been confirmed that still another value should be taken into consideration, that is a maximum adhesion water percentage $\beta$max which is the maximum percentage of water capable of depositing on the surface of fine aggregate.

According to one aspect of the invention there is provided a method of preparing mortar or concrete by utilizing a powder of hydraulic compound, fine aggregate (and coarse aggregate, if the case may be) and water, characterized in that a percentage of water contained in or adhered to the fine aggregate corresponding to the JIS surface-dry water percentage, minimum and maximum adhesion water percentages and a percentage of water of the fine aggregate in which interstice thereof is saturated with water while the surface is dry are determined respectively, and a quantity of water to be added for preparation of the mortar or concrete is determined according to the minimum adhesion water percentage multiplied by a predetermined multiplier, which method is capable of preparing mortar or concrete having an improved mechanical strength.

According to another aspect of the invention there is provided a method of measuring the minimum and maximum adhesion water percentages and the interstice-saturated water percentage of the fine aggregate respectively, characterized by prewetting the fine aggregate, by containing the fine aggregate in an air-tightly closed container, by applying a centrifugal force to the container over a predetermined period to remove a portion of a quantity of water contained in or adhered to the fine aggregate, and by measuring water content remaining in or on the fine aggregate after being subjected to the centrifugal force. By this method it will be possible to recognize characteristics of the fine aggregate used in preparation of mortar or concrete.

According to still another aspect of the invention there is provided a device for measuring the minimum and maximum adhesion water percentages and the interstice-saturated water percentage of the fine aggregate comprising an air-tightly closed tubular container provided therein with a filter which divides the container into a first one-half portion adapted to accomodate the prewetted fine aggregate and a second one-half portion adapted to contain a water absorption material and a rotary plate which rotatably supports the tubular container at the central portion thereof, whereby a centrifugal force created by rotation of the rotary plate is applied to the fine aggregate contained in the tubular container. Use of this device will lead to accurate measurement in a short period of time.

BRIEF DESCRIPTION OF DRAWINGS

FIG. 2 is an exploded view, partly in section and partly in plan, of a preferred embodiment of a devide for measuring percentages of the aggregate according to this invention;

FIG. 3 is a sectional view showing the device of FIG. 2 being assembled into a unit;

FIG. 4 is a sectional view showing a test apparatus in which the device of FIG. 3 is used;

PREFERRED EMBODIMENTS OF THE INVENTION

Figure 1:
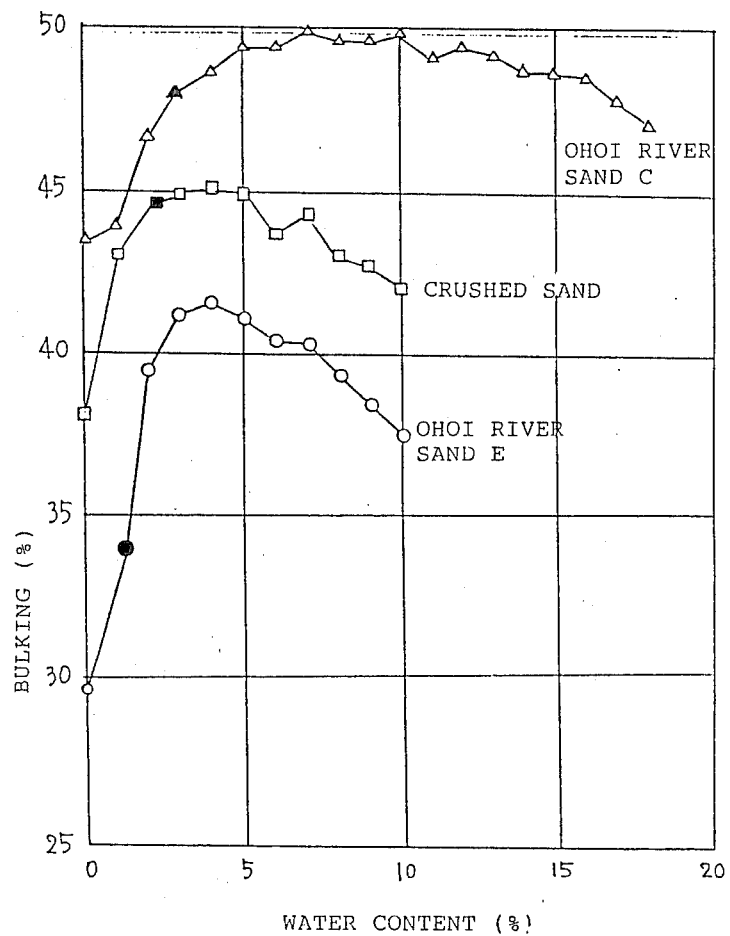
FIG. 1 is a graph showing relationship between water content and percentage of bulking of various fine aggregate having different JIS surface-dry water percentages.

The invention will now be described in more detail while referring to FIGS. 2 through 16.

FIG. 2 shows a preferred embodiment of a device for measuring various water percentages of fine aggregate to be used in preparation of mortar or concrete, that is characteristics of the fine aggregate which will greatly influence the quality of the resulting mortar or concrete. Since it is essential to measure in a short available period of time, with efficiency, the JIS surface-dry water percentage Q, the minimum adhesion water percentage $\beta$lim, the maximum adhesion water percentage $\beta$max and the interstice-saturated water percentage $Q_0$, it is herein proposed to accomodate pre-wetted fine aggregate in a closed container which is then subjected to a centrifugal force. More particularly, as shown in FIG. 2, the device comprises first and second cylindrical members 10,10 having length of 10 cm and 5 cm respectively and each composed of a vinyl chloride tube having a diameter of 5 cm one open end of which is closed by an acrylic resin plate 11, and a wire net 12 made of metal wires having a diameter of 0.15 mm, a paper filter 13 and a steel plate 14 of 1.6 mm thickness having a plurality of perforations which are interposed between the first and second cylindrical members. To the first cylindrical member is charged 200 g of a test sample of fine aggregate while the second cylindrical member 10 is filled with an absorbent cotton 16. They are oppositely joined as shown in FIG. 3 with a vinyl tape 15 for establishing air-sealed condition. The cylindrical unit thus assembled is then received in a case 20 which can be sealed by a cover 21, more particulalry the major part of the unit is received in a carriage 24 pivottably connected via an axis 25 to a rotary plate 22 provided in the case 20, thereby creating a centrifugal force by rotation of the rotary plate 22. A quantity of water is removed from the fine aggregate in the first cylindrical member and absorbed into the absorbent cotton 16 in the second cylindrical member with the centrifugal force applying treatment, but the water thus absorbed into the absorbent cotton 16 is prevented from returning into the first cylindrical member after the treatment is completed to stop the rotary plate 22 from rotation.

For the purpose of determining accurate values of the minimum adhesion water percentage $\beta$lim and the interstice-saturated and surface-dry water percentage Q, it is important that the cylindrical members 10,10 are assembled into an air-sealed unit by using the vinyl tape 15 or the like. If a centrifugal force is applied to a container provided with no air-sealing means, air in the container is removed to the outside to thereby reduce the inner pressure and air flows repeatedly between the inside and the outside of the container, which would result in evaporation of water in the container. In order to prevent such evaporation of water due to the air flow, the assembled unit of the cylindrical members 10,10 should be air-tightly sealed to assure accurate results of the measurement.

A sand sample E collected in the Ohoi River (fineness modulus FM=3.23, bulking $\epsilon$=33.8%) having 1.39% of the value Q measured according to the method of JIS A1109 was treated with the above described device. More particularly, this sample was pretreated by drying for 24 hours at a temperature of 110° C. followed by addition of water thereto in a vacuum mixer with a pressure of $-730$ mmHg so that water was deposited to the respective samples in different quantities ranging from 1Q to 10Q, and then they were subjected to a centrifugal force of 4.53 g (g:acceleration of gravity) for 120 minutes to remove a portion of the deposited water. The results of the test are shown in FIG. 5 in which the abscissa showing the treating period is given as a logarithmic scale.

Figure 5:
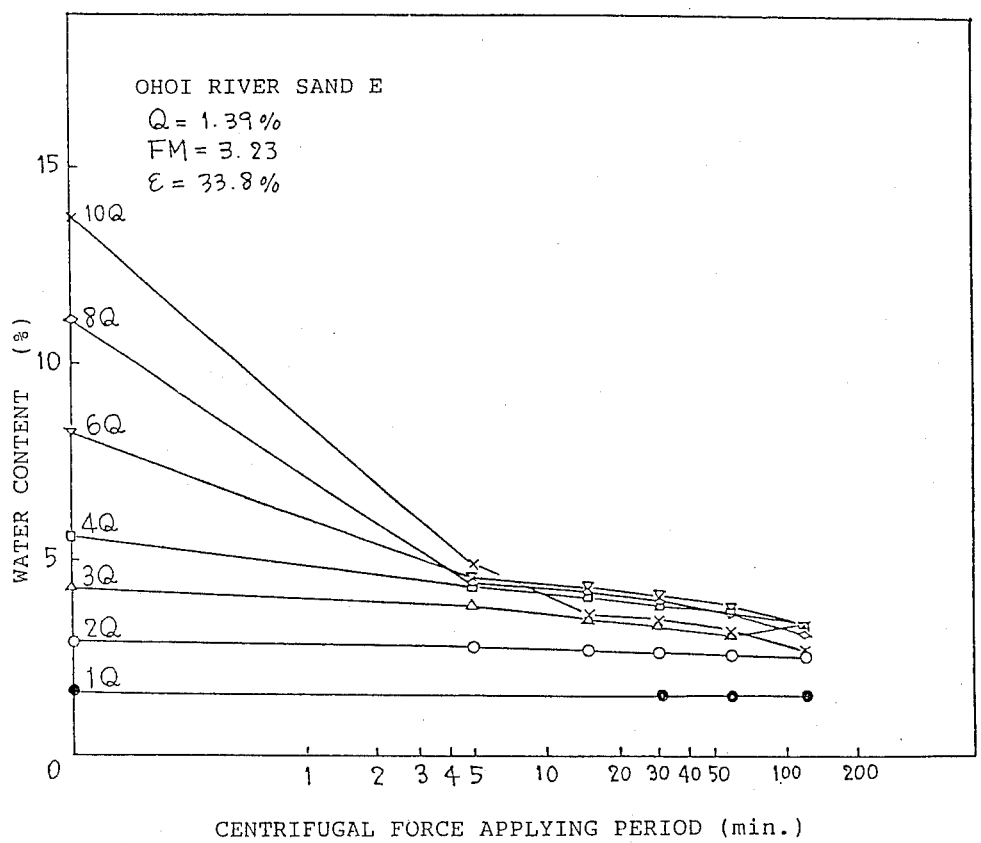
FIG. 5 is a graph showing relationship between a centrifugal force applying period and water content when the measurement of this invention is applied to fine aggregate whose initial water content are made different.
Figure 6:
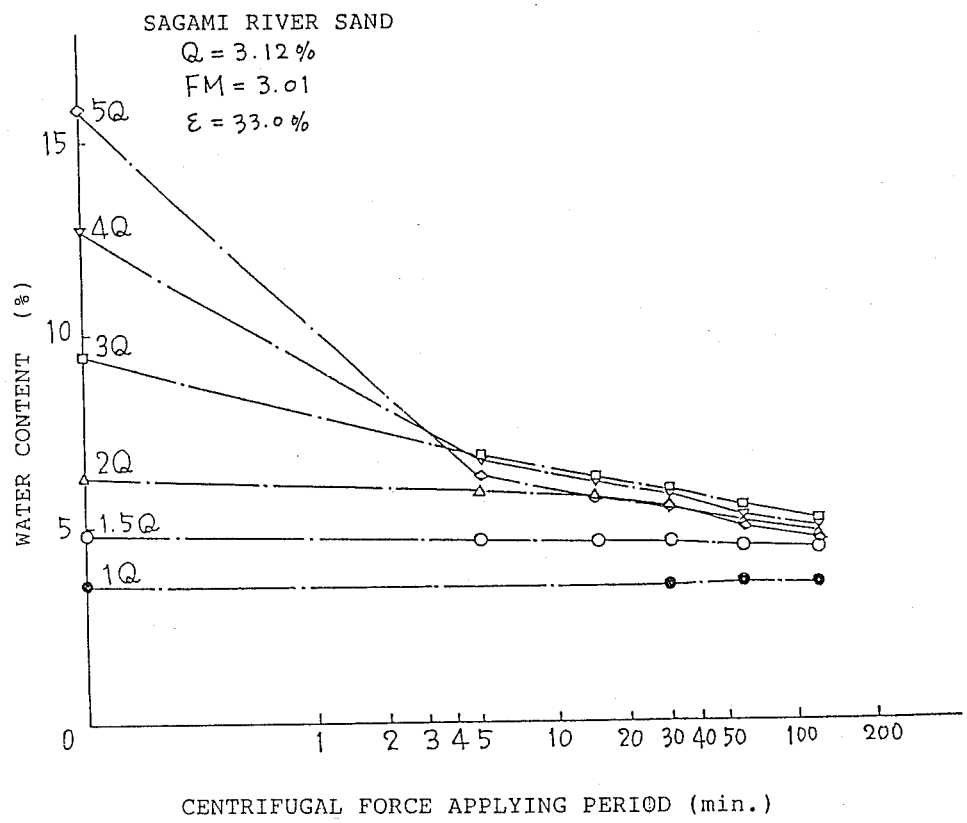
FIG. 6 is a graph showing the results of measurement carried out in the same manner as in FIG. 5 with respect to other types of fine aggregate.

As shown in FIG. 5, the water content of samples which initially had the water content of less than 5Q is reduced substantially proportional to the centrifugal force applying period, and the water content of a sample having the initial water content of 1Q remains substantially unchanged irrespective of the treating period. On the other hand, the water content of samples having the initial water content of 6Q or larger is considerably reduced in the first 5 minutes, but the reduction of water content past 5 minutes is paced down, which is equivalent to samples having the initial water content of 4Q or smaller. In other words, the reduction pace of water content of samples having the initial water content of 6Q or larger is apparently different between prior and past a certain changing point on the abscissa shown by a logarithmic scale. It can be assumed that the maximum initial water content of a sample in which such a changing point is not noted is identified with the maximum adhesion water percentage $\beta$max, and the water content in excess of the maximum adhesion water percentage may be readily separated from the fine aggregate while the water separation effect is decelerated when the water content becomes smaller than the maximum adhesion water percentage. This can be also said to other kinds of sand. For example, another test was made in the same manner regarding a sand collected in the Sagami River having FM=3.01, bulking $\epsilon$=33.0% and the Q value according to JIS A1109 of 3.12% which is considerably greater than that of the sand sample E used in the preceeding test shown in FIG. 5, and the results of this test are shown in FIG. 6. As shown, the water content of this Sagami River sand is proportionally lowered when the initial water content is 3Q or smaller, but in the case of 4Q or more there is noted a changing point at 5 minutes centrifugal force applying treatment, meaning that the maximum adhesion water percentage βmax of this sample sand is about 3Q.

Figure 7:
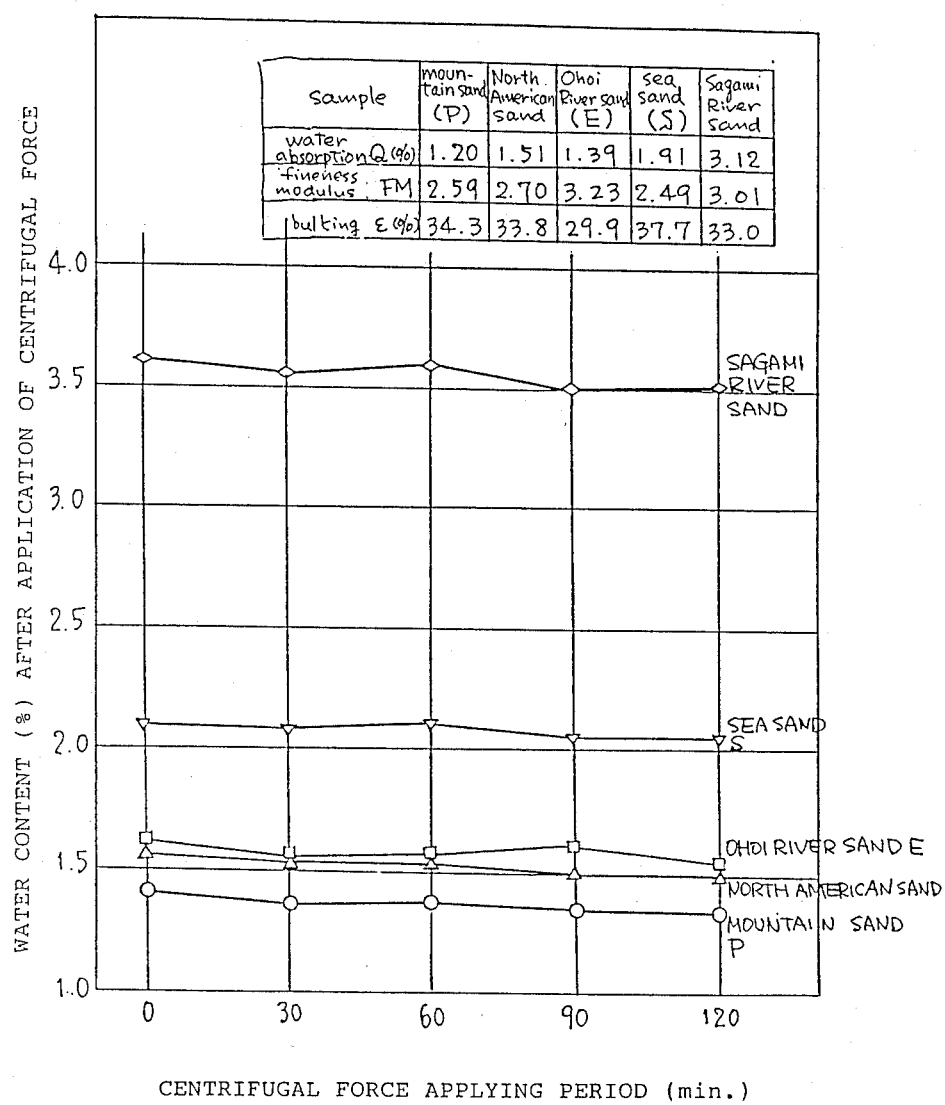
FIG. 7 is a graph showing the results of the centrifugal force applying test applied to various types of fine aggregate having an initial water content of about 1Q.

FIG. 7 shows the results of the centrifugal force applying test in the same manner regarding the principal five kinds of fine aggregate including the aforesaid two kinds which were pretreated to have the initial water content of about 1Q. In all samples, the water content remained substantially unchanged irrespective of treating period of the separation test. This result would lead to the conclusion that the water content Q measured according to JIS A1109 is reliable and substantially constant. However, a water quantity that influences characteristics (bleeding, fluidability, etc.) of a resulting mixture will be larger than Q, and still larger than the maximum adhesion water percentage βmax so long as we suppose by the results shown in FIGS. 5 and 6.

Figure 8:
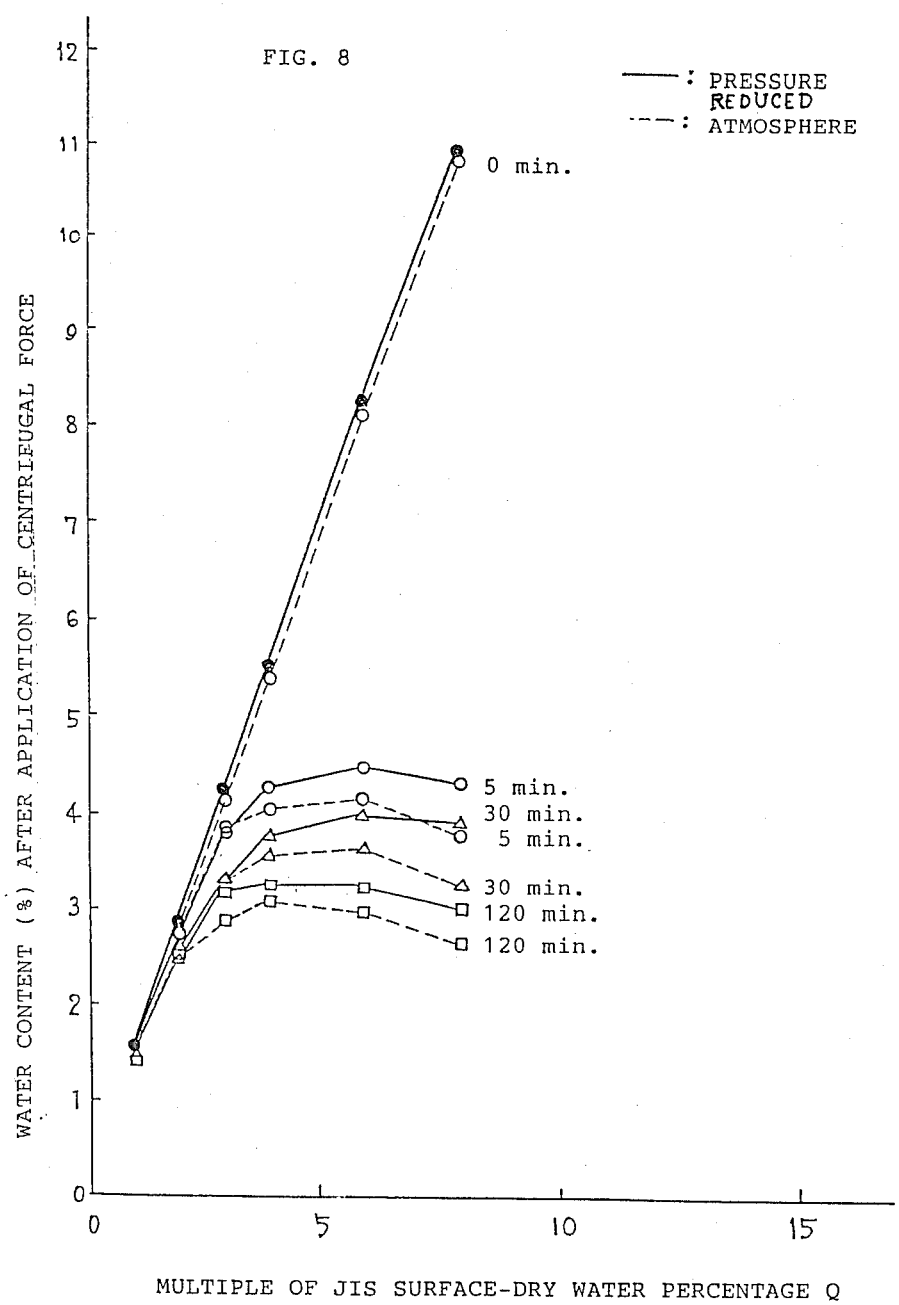
FIG. 8 is a graph showing the results of the centrifugal force applying test in which water is added under an atmospheric condition and a pressure reduced condition respectively.

In the measurement test above described, it is essential to add water in the pressure reduced condition to thereby shorten the period required for measurement. More particularly, when creating a pressure condition reduced to −730 mmHg, for example, an air void or film on the surface of the fine aggregate is effectively removed, and when water is then added thereto in this pressure reduced condition the added water is absorbed into the interstice of the fine aggregate and uniformly deposited on the surface thereof. On the other hand, if water should be added in the atmospheric condition there would be a possibility that water is eccentrically and not uniformly deposited on the surface, which may cause the result of measurement to vary and become unreliable. For example, regarding the absolutely-dry sand sample E collected in the Ohoi River, one was incorporated with water in a vaccum mixer in the above pressure reduced condition and the other in the atmosphere, and then both samples were subjected to the centrifugal force applying treatment to remove excess water. The results is shown in FIG. 8 showing that there is a difference in water content of two samples with the same period of treatment, namely the same period of treatment reduced the water content of the sample to which water had been added in the atmosphere to a value smaller than that of the other sample. Repeated tests revealed that the results of the sample to which the pressure reduced treatment had been applied were substantially constant. Similar results were obtained with respect to other kinds of fine aggregate, the Sagami River sand, a granulated slag sand and an ordinary sand.

Moreover, eleven kinds of fine aggregate were pretreated to adjust their initial water content to a value corresponding to 3Q and then subjected to a contrifugal force of 4.53 g for water separation test. The results are shown in the following Table I.

TABLE I

| | kind | 1 granulated slag sand A produced in Hirohata | 2 mountain sand F | 3 F sand produced in Ohoi River | 4 granulated slag sand B produced in Nagoya | 5 E sand produced in Ohoi River | 6 crushed sand (8204) |
|---|---|---|---|---|---|---|---|
| characteristics | water absorption Q (%) | 0.64 | 1.20 | 1.20 | 1.29 | 1.39 | 1.48 |
| | fineness modulus FM | 2.57 | 2.51 | 2.82 | 2.30 | 3.23 | 2.86 |
| | bulking ε (%) | 34.3 | 32.1 | 32.8 | 40.8 | 29.9 | 36.4 |
| 3 × Q = SW₀ (%) | | 1.92 | 3.60 | 3.60 | 3.87 | 4.17 | 4.44 |
| treating period (min) | | water content (%) | | | | | |
| results | 0 | 1.58 | 3.82 | 3.26 | 3.64 | 3.76 | 4.03 |
| | 30 | 1.46 | 3.31 | 3.00 | 3.16 | 3.42 | 3.68 |
| | 60 | 1.38 | 2.82 | 2.76 | 2.85 | 3.13 | 3.27 |
| | 90 | 1.26 | 2.73 | 2.61 | 2.58 | 2.81 | 3.03 |
| | 120 | 1.20 | 2.50 | 2.41 | 2.56 | 2.81 | 2.90 |

| | | 7 sand produced in the North America | | 8 sea sand S | 9 crushed sand | 10 C sand produced in Ohoi River | 11 river sand (Sagami River) | | |
|---|---|---|---|---|---|---|---|---|---|
| | kind | 1st. | 2nd. | | | | 1st. | 2nd. | 3rd. |
| characteristics | water absorption Q (%) | 1.51 | 1.51 | 1.91 | 2.30 | 2.84 | 3.12 | 3.12 | 3.12 |
| | fineness modulus FM | 2.70 | 2.70 | 2.49 | 2.94 | 1.40 | 3.01 | 3.01 | 3.01 |
| | bulking (%) | 33.8 | 33.8 | 37.7 | 32.8 | 39.7 | 33.0 | 33.0 | 33.0 |
| 3 × Q = SW₀ (%) | | 4.53 | 4.53 | 5.73 | 6.90 | 8.52 | 9.36 | 9.36 | 9.36 |
| treating period (min) | | water content (%) | | | | | | | |
| results | 0 | 4.10 | 4.53 | 5.27 | 7.22 | 9.14 | 9.15 | 9.15 | 9.15 |
| | 30 | 2.87 | 2.83 | 4.84 | 5.49 | 7.40 | 5.96 | 5.91 | 6.07 |
| | 60 | 2.48 | 2.54 | 4.42 | 5.08 | 7.06 | 5.37 | 5.73 | 5.56 |
| | 90 | 2.29 | 2.44 | 4.08 | 4.76 | 6.65 | 4.97 | 5.35 | 5.35 |
| | 120 | 2.21 | 2.29 | 3.86 | 4.58 | 6.50 | 4.93 | 5.24 | 5.23 |

Figure 9:
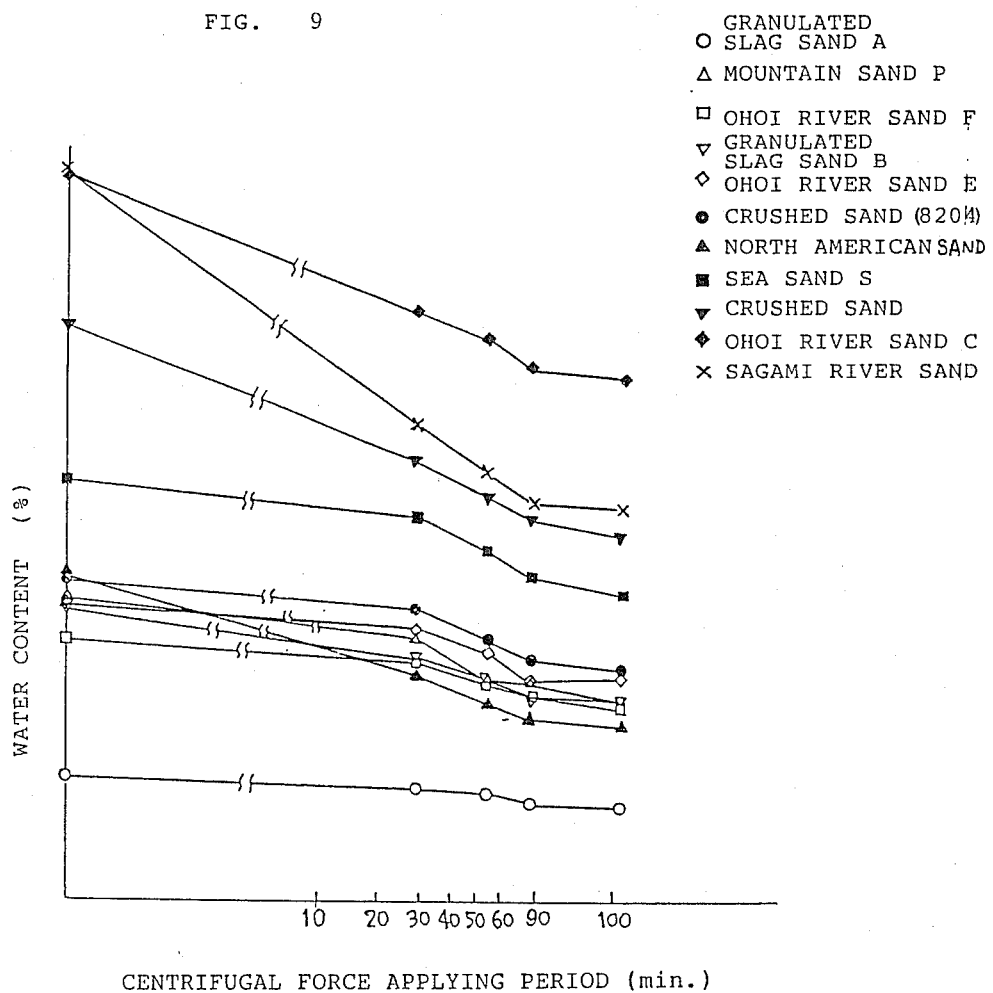
FIG. 9 is a graph showing relation between a centrifugal force applying period and water content with respect to various types of fine aggregate.

The results are also shown in a graph of FIG. 9. As can be noted from Table I and FIG. 9, the initial water content 3Q (which is shown in FIG. 9 by a coordinate existing on the ordinate at the treating period of zero) of each fine aggregate is lowered with the passage of period of centrifugal force applying treatment, and as far as the samples other than the Sagami River sand and the sand produced in the North America the water content thereof were reduced substantially in proportion to the treating period and lowered to a value twice the JIS surface-dry water percentage Q after 120 minutes treatment. Fineness modulus and bulking would not affect the water separation effect.

Figure 10:
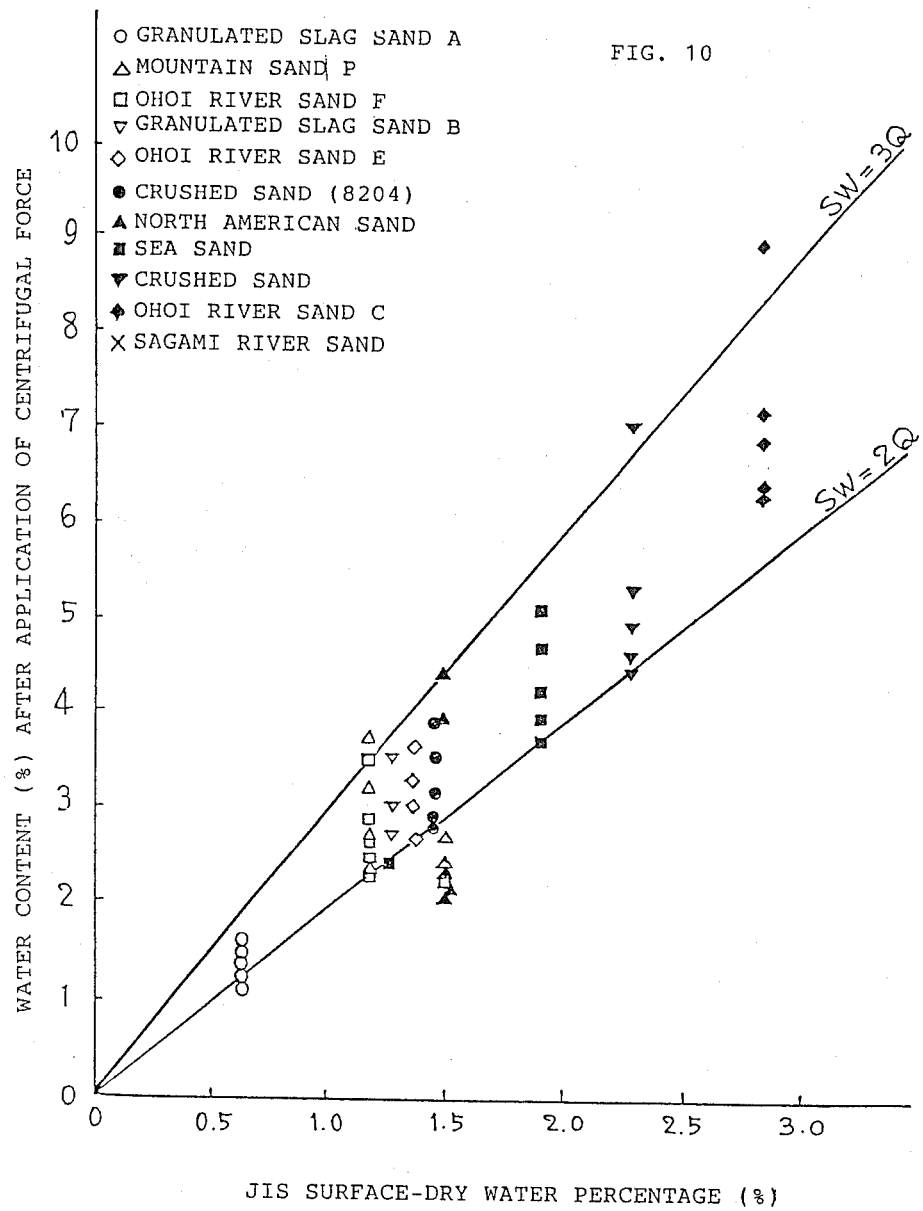
FIG. 10 is a graph showing relation between the water content shown in FIG. 9 and the value Q.
Figure 11:
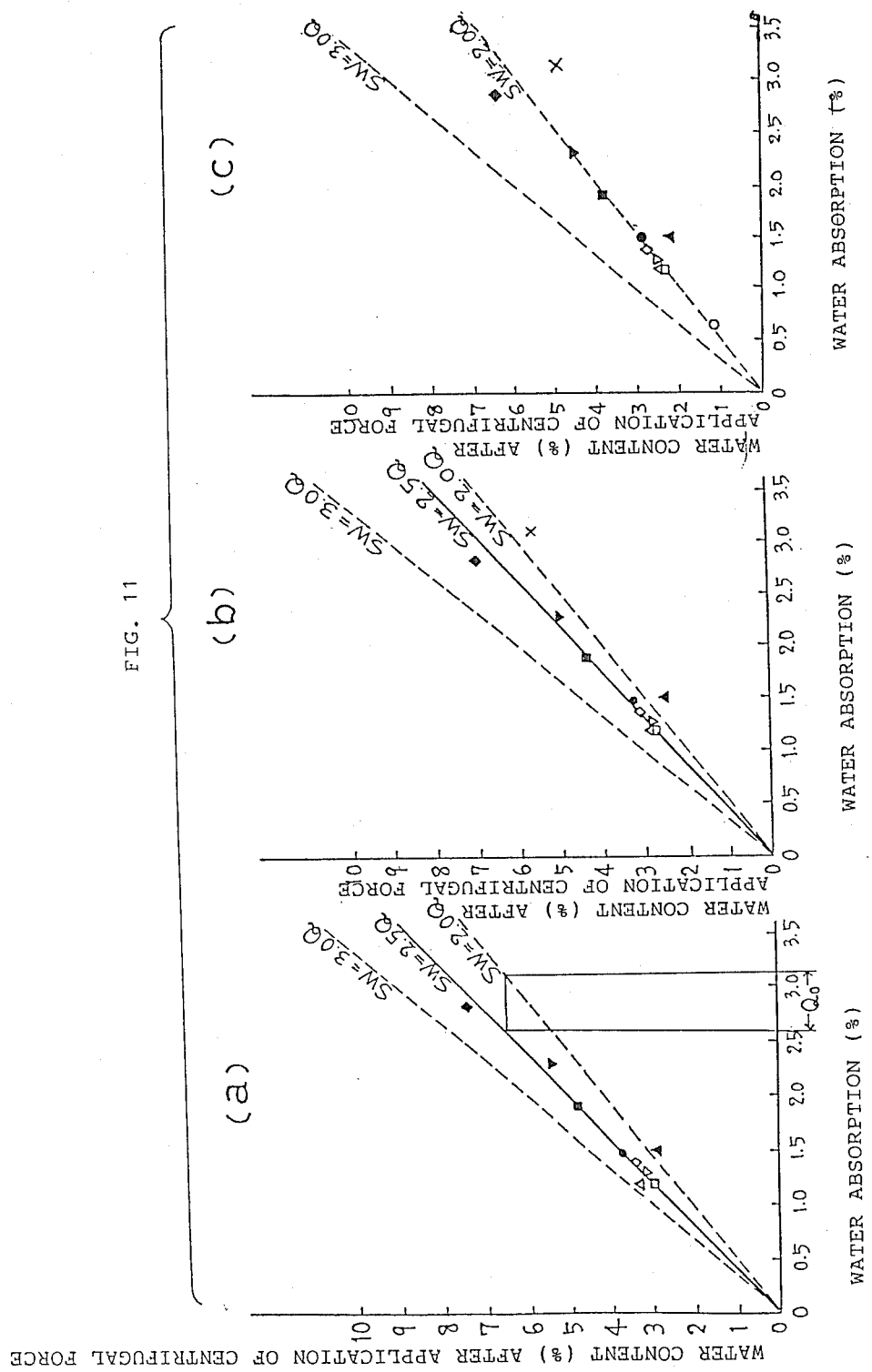
FIG. 11 is a graph showing the same relation, per centrifugal force applying period of 30 min., 60 min. and 120 min. respectively.

FIG. 10 shows the above test results in relation to the JIS surface-dry water percentage Q showing that the water content after treatment is proportionally correlated with Q, which is shown in more detail in FIGS. 11A–11C. More particularly, the relation between the water content (%) SW after treatment and Q value of the fine aggregate can be expressed by SW=2.5Q, SW=2.3Q and SW=2.0Q with the centrifugal force applying treatment over 30 minutes, 60 minutes and 120 minutes, respectively. Meanwhile, the reason why there are some kinds of fine aggregate such as the Sagami River sand and the North American sand in which the relation between SW and Q is not always proportional would be because of a substantial value of the interstice-saturated water content $Q_0$ of the fine aggregate. Thus, most of samples have $Q_0$ being nearly zero which can be practically disregarded so that the proportional relation between the water content SW and Q value can be obtained, but such a proportional relation is not applied to some kind of fine aggregate due to its non-negligible value of $Q_0$. For example, as shown in FIG. 11A the water content SW of the Sagami River sand after 30 minutes treatment is larger by about 0.55% than a standard value determined by SW=2.5Q, which percentage of 0.55% could be regarded as $Q_0$ of the Sagami River sand. Since 30 minutes centrifugal force applying treatment is enough to determine the relation between SW and Q, the period of treatment should preferably be 30 minutes for shortening the test time as much as possible.

Now, consideration of the relation between the maximum surface-adhesion water percentage $\beta max$ and the minimum surface-adhesion water percentage $\beta lim$ will be given hereunder. More particularly, both define the quantity of water or thickness of water film deposited on the surface of fine aggregate, but when it is difficult or physically impossible to deposit water on the surface in a quantity smaller than a certain critical value, then this critical value will equal to the minimum water percentage $\beta lim$, whereas when it is difficult or physically impossible to deposit water in a quantity larger than another certain critical value, then this critical value will be equivalent to the maximum water percentage $\beta max$. Water can be deposited on the sand surface in a percentage ranging from $\beta lim$ to $\beta max$. It can stood that $\beta max$ is represented by $\beta lim$ multiplied by a certain multiple A, and the JIS surface dry water percentage Q is expressed by $Q=\beta lim+Q_0$ as described before, so that we obtain the following equation I:

$$\beta max = A \cdot \beta lim = A(Q-Q_0) \qquad \text{I}$$

The measured value $\beta z$ at the changing point which can be obtained in a relatively short period of time by the centrifugal force applying treatment can be represented by the following equation II:

$$\beta z = A \cdot \beta lim + Q_0 \qquad \text{II}$$

The equations I and II will lead to:

$$Q_0 = \frac{AQ - \beta z}{A - 1} \qquad \text{III}$$

Then, $Q_0$ can be determined according to the equation II, and when $Q_0$ is determined $\beta lim$ and $\beta max$ can be determined according to the equations I and II respectively ($\beta max = \beta z - Q_0$).

While $Q_0$ can be obtained in theory according to the equation III, it is nevertheless necessary to determine the multiple A of the fine aggregate. This value may be obtained by using a simulated test sample having $Q_0=0$ such as artificial glass piece and steel pellet and measuring $\beta lim$ and $\beta max$ thereof. The resulting value thus obtained, however, can not be always applied to the fine aggregate to be used in practice for preparing mortar or concrete. Moreover, such an artificial test piece having $Q_0=0$ can not be readily available and in most case contains a number of perforations or hollows which would be inevitably formed, resulting in lesser reliability of the obtained value A.

Accordingly, in this invention a sand sample having $Q_0$ of approximately zero is regarded as a standard sample having $Q_0=0$, for convenience. In the strict sense the result of the test obtained by using such a sample is not identical with the real value A because of $Q_0 \neq 0$, but will fall within a permissible error range. Thus, various kinds of test samples are subjected to the centrifugal force applying treatment so as to obtain the water content z, and the value z is divided by the JIS surface dry water percentage Q (actually measured; but can be replaced by Q' as described before), thereby obtaining the value $\beta z/Q$ respectively. Then, the test sample having the largest value $\beta z/Q$ will be entitled to the standard test sample whose interstice saturated percentage $Q_0$ can be considered to be substantially zero. Regarding other samples having smaller value of $\beta z/Q$, the interstice-saturated water percentage $Q_0$ thereof is defined by the difference between the water content actually measured and that determined according to the obtained value $\beta z/Q$ of the standard test sample. When Q, $Q_0$ and $\beta z$ are thus determined, the multiple A can be obtained in accordance with the equation III and then $\beta lim$ can be obtained by the equation I. Generally, A is a value ranging from 2 to 7, more specifically from 2 to 5.

In mortar or concrete prepared by utilizing fine aggregate and powder of hydraulic compound there exists a cement paste among particles of fine aggregate. In other words, mortar or concrete comprises the cement paste and sand particles (water and additives, if any, are adhered to the surface thereof) in a mixed state. Accordingly, the water quantity $W_1$ existing in the primary kneading operation in the double kneading process disclosed in Japanese Patent Publication No. 104958/1980 and in the U.S. Pat. No. 4,299,633 can be divided into two portions, one in the paste and the other in or on the sand particles. Where a quantity of water in the paste is shown by Wp, the ratio $W_1/C$ at the time of the primary kneading can be represented by the following equation IV:

$$W_1/C = Wp/C + \beta_0 \cdot S/C \qquad \text{IV}$$

In the above equation IV, $\beta_0$ is a quantity of water deposited on the sand particles, which can be expressed by $\beta max + Q_0$, as having been described, in the most stable phase. On the other hand, the water quantity in the cement paste Wp will be preferably determined in accordahce with the method disclosed in Japanese Patent Publication No. 56815/1983 wherein a quantity of the primary water is controlled so as to cause the cement paste to be in a fanicular region or a slurry region close to the capillary state. More specifically, the torque required for kenading the cement paste is considerably high when the cement paste has W/C ration of 15–38%, especially about 24% in the case of using the ordinary Portland cement. Thus, the water quantity Wp can be determined based on Wp/C ratio falling within such a range.

For better understanding of the invention the following examples will be given.

EXAMPLE 1

Various kinds of sand shown in the following Table II were prepared. Regarding the multiple A, the Ohoi River sand sample F and mountain sand samples P and K were regarded as the standard samples having $Q_0$ of nearly zero so that the values A' were assumed to be 2.50, 2.76 and 2.86 respectively. Each sample was mixed with a powder of ordinary Portland cement with a ratio of sand to cement (S/C)=2 in a volume scale, to thereby prepare a mortar.

was minimized at the multiple A of about 4, and more specifically when the value A to be multiplied by $\beta$lim is selected to be in a range of 2-7 it becomes possible to prepare a mortar without substantial quantity of bleeding.

Figure 12:
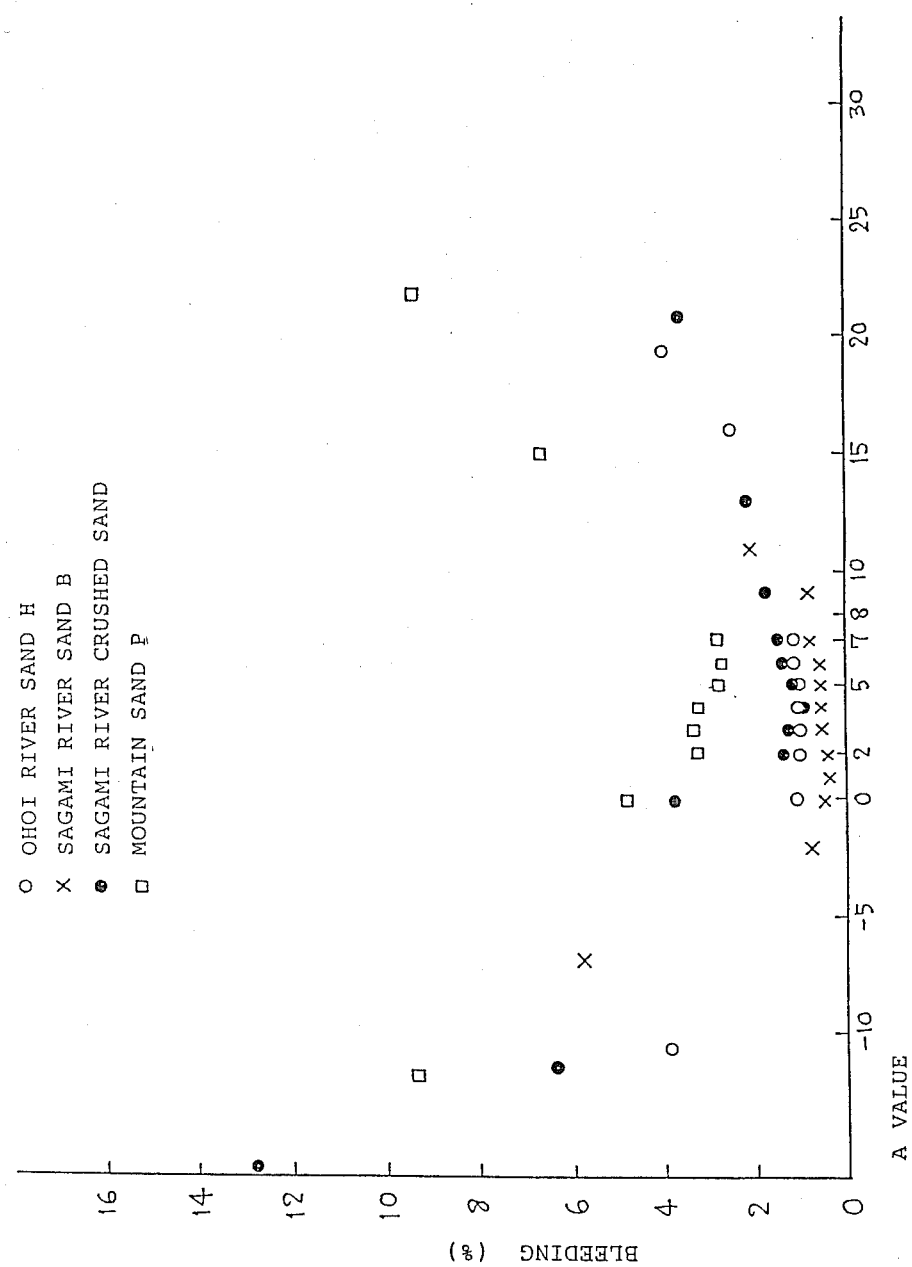
FIG. 12 is a graph showing the results of measurement of bleeding in accordance with the method prescribed in JIS regarding mortars prepared by using various types of fine aggregate to which primary water in different quantities are added (that is, multiples of $\beta$lim are varied) followed by first and second kneading operation.
Figure 13:
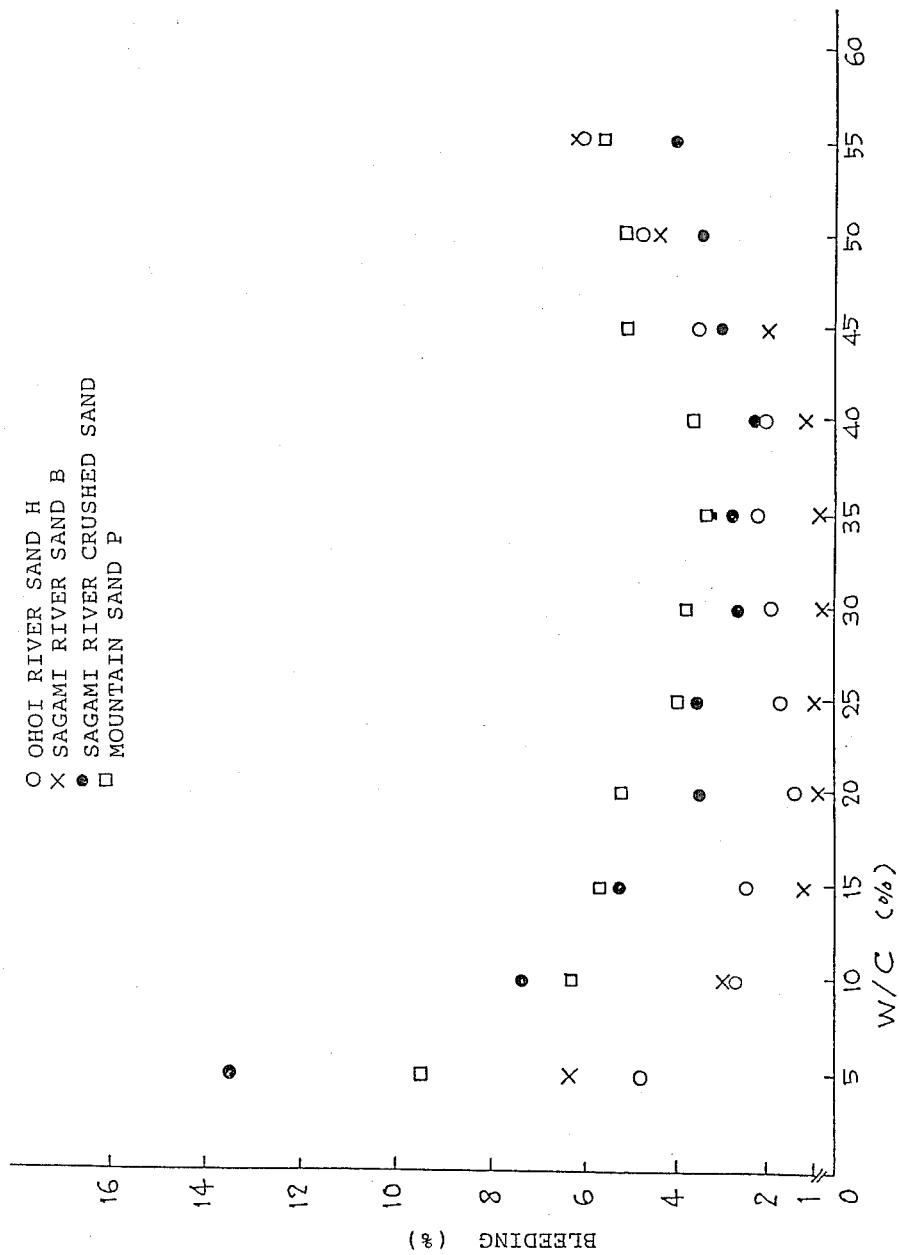
FIG. 13 is a graph showing the results of measurement of bleeding in the same manner as in FIG. 12, regarding mortars prepared by the prior art method based on the JIS surface-dry state.

In the meantime, the same four samples as used in the above test of FIG. 12 were used to prepare mortars according to the conventional method in which the JIS surface-dry water content Q is considered to be ineffective for the quality or properties of the resulting mixture, and the bleeding of the resulting mortars were measured in the same manner. The results are shown in FIG. 13. Generally, the bleeding percentage was larger (by about 0.5% at the minimum) than the results shown in FIG. 12. Moreover, the quantity of the primary water which would be most effective to reduce the bleeding

TABLE II

| characteristics | | granulated slag sand A | sand produced in the North America | mountain sand K | C sand produced in Ohoi River | sand produced in Tenbayama | mountain sand P |
|---|---|---|---|---|---|---|---|
| FM | | 2.54 | 2.70 | 2.51 | 2.82 | 2.76 | 2.51 |
| surface-dry specific gravity | | 2.84 | 2.63 | 2.63 | 2.63 | 2.65 | 2.63 |
| absolute-dry specific gravity | | 2.82 | 2.59 | 2.59 | 2.60 | 2.58 | 2.62 |
| bulking $\epsilon$ | | 34.3 | 33.8 | 31.3 | 32.8 | 33.1 | 32.1 |
| water absorption Q (JIS surface-dry) | | 0.64 | 1.51 | 0.84 | 1.20 | 2.01 | 1.20 |
| water content $\beta z$ (415 g, 30 minutes) | | 1.46 | 2.85 | 2.40 | 3.00 | 4.10 | 3.31 |
| A' 2.50 | $Q_0$ $\beta$lim | 0.09 0.55 | 0.62 0.89 | −0.20 1.04 | 0 1.20 | 0.62 1.39 | −0.21 1.41 |
| A' 2.76 | $Q_0$ $\beta$lim | 0.17 0.47 | 0.75 0.76 | −0.05 0.89 | 0.18 1.02 | 0.82 1.19 | 0 1.20 |
| A' 2.86 | $Q_0$ $\beta$lim | 0.20 0.44 | 0.79 0.72 | 0 0.84 | 0.23 0.97 | 0.89 1.12 | 0.07 1.13 |

| characteristics | | G sand produced in Ohoi River | Sagami River crushed sand | H sand produced in Ohoi River | Sagami River sand A | sea sand S | Sagami River sand B | C sand produced in Ohoi River |
|---|---|---|---|---|---|---|---|---|
| FM | | 2.75 | 2.85 | 2.56 | 3.01 | 2.49 | 3.00 | 1.40 |
| surface-dry specific gravity | | 2.63 | 2.62 | 2.58 | 2.60 | 2.59 | 2.60 | 2.53 |
| absolutely-dry specific gravity | | 2.59 | 2.59 | 2.54 | 2.54 | 2.54 | 2.51 | 2.47 |
| bulking $\epsilon$ | | 29.5 | 36.3 | 32.0 | 33.0 | 37.7 | 30.0 | 39.7 |
| water absorption Q (JIS surface-dry) | | 1.42 | 1.23 | 1.70 | 3.12 | 1.91 | 3.59 | 2.84 |
| water content $\beta z$ (415 g, 30 minutes) | | 3.54 | 3.49 | 4.01 | 5.98 | 4.84 | 7.30 | 7.40 |
| A' 2.50 | $Q_0$ $\beta$lim | 0.01 1.41 | −0.28 1.51 | 0.16 1.54 | 1.21 1.91 | −0.04 1.95 | 0.08 2.49 | −0.20 3.04 |
| A' 2.76 | $Q_0$ $\beta$lim | 0.22 1.20 | −0.05 1.28 | 0.39 1.31 | 1.50 1.62 | 0.25 1.66 | 1.45 2.12 | 0.25 2.59 |
| A' 2.86 | $Q_0$ $\beta$lim | 0.28 1.14 | 0.01 1.22 | 0.46 1.24 | 1.58 1.54 | 0.33 1.58 | 1.56 2.01 | 0.39 2.45 |

Among these samples the Ohoi River sand H, the Sagami River sand B, the Sagami River crushed sand and the mountain sand P were used to prepare mortar respectively according to the double kneading process in which a necessary quantity of water is divided into primary and secondary portions of water. The bleeding of the resulting mortars were measured according to the method of JIS A1123 to obtain the results shown in FIGS. 12. In this test, the water to cement ratio (W/C) of the cement paste was determined to be 24%, and the quantity of the primary water was determined based on the A' values which was variously varied as shown. The mountain sand P was regarded as a standard sample having $Q_0$ of nearly zero. It can be noted from the results shown in FIG. 12 that the bleeding appearance of the resulting mortar was quite different for the respective sand samples, that is W/C=20% for the Ohoi River sand F, 30% for the Sagami River sand B, 40% for the Sagami River crushed sand and 35% for the mountain sand P, respectively.

Figure 14:
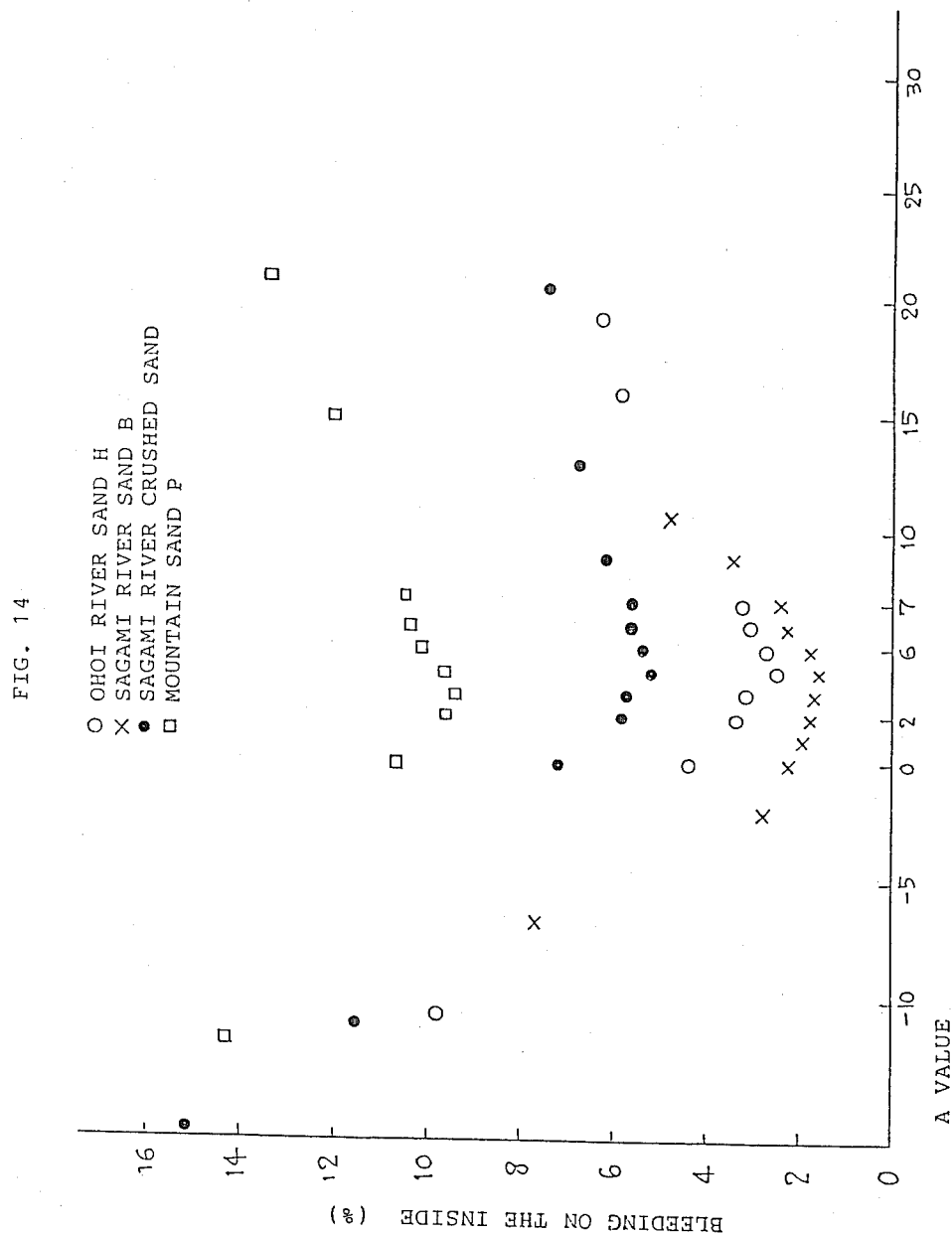
FIG. 14 is a graph showing the results of measurement of bleeding in accordance with a novel method which we have proposed regarding mortars prepared by using the same sand and same quantities of primary water as in FIG. 12.
Figure 15:
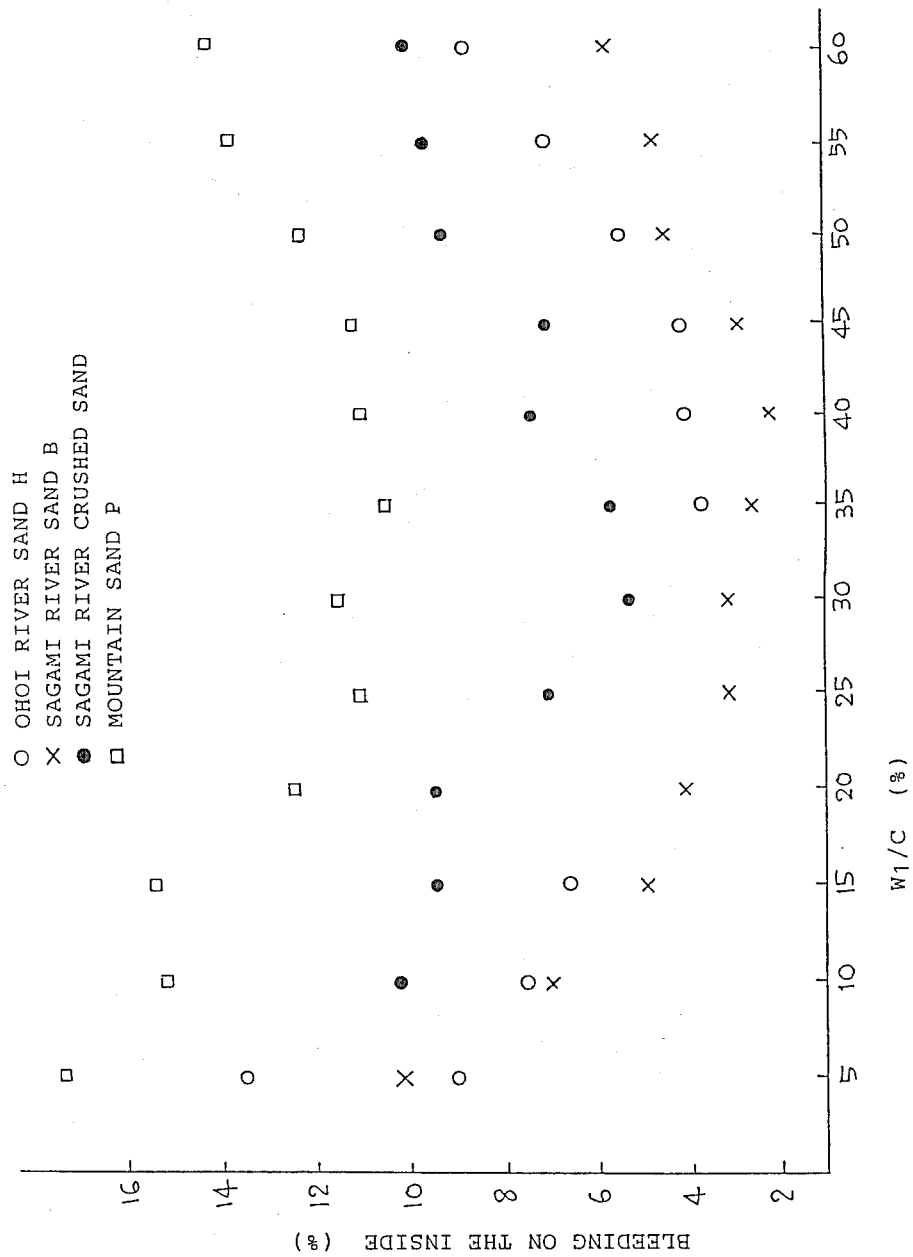
FIG. 15 is a graph showing the results of measurement of bleeding in accordance with the novel method regarding mortars prepared by the prior art method based on the JIS surface-dry state.

While FIGS. 12 and 13 show the bleeding measured in accordance with the method of JIS A1123, the bleeding of the respective mortars resulting from the same samples were also measured by another method that we have already proposed in Japanese Patent Publication No. 162867/1983. As shown in FIG. 14, according to the method of the invention the bleeding of each mortar was reduced to the minimum at A=4 (while the minimum bleeding was obtained at A=3 for the mountain sand P), and it can be noted that when selecting the multiple A to be in a range of 2–7 the resulting mortars can be substantially free from bleeding, as in the case of FIG. 12. FIG. 15 shows the results similar to those in FIG. 13, more particularly the bleeding was generally larger than in FIG. 14, and the minimum bleeding could be established in different W/C ratios for respective samples, that is W/C=25% for the Ohoi River sand F, 40% for the Sagami River sand B, 30% for the Sagami River crushed sand and 35% for the mountain sand P, respectively. Let us say in more detail about two methods for measuring the bleeding, in the unique method that we proposed the bleeding is measured inside the mixture whereas in the method of JIS A1123 a quantity of bleeding water separated from the mixture to float on the upper face thereof is measured, so that the measurement by the former method will bring a greater value and more reliable results than the latter JIS A1123.

Figure 16:
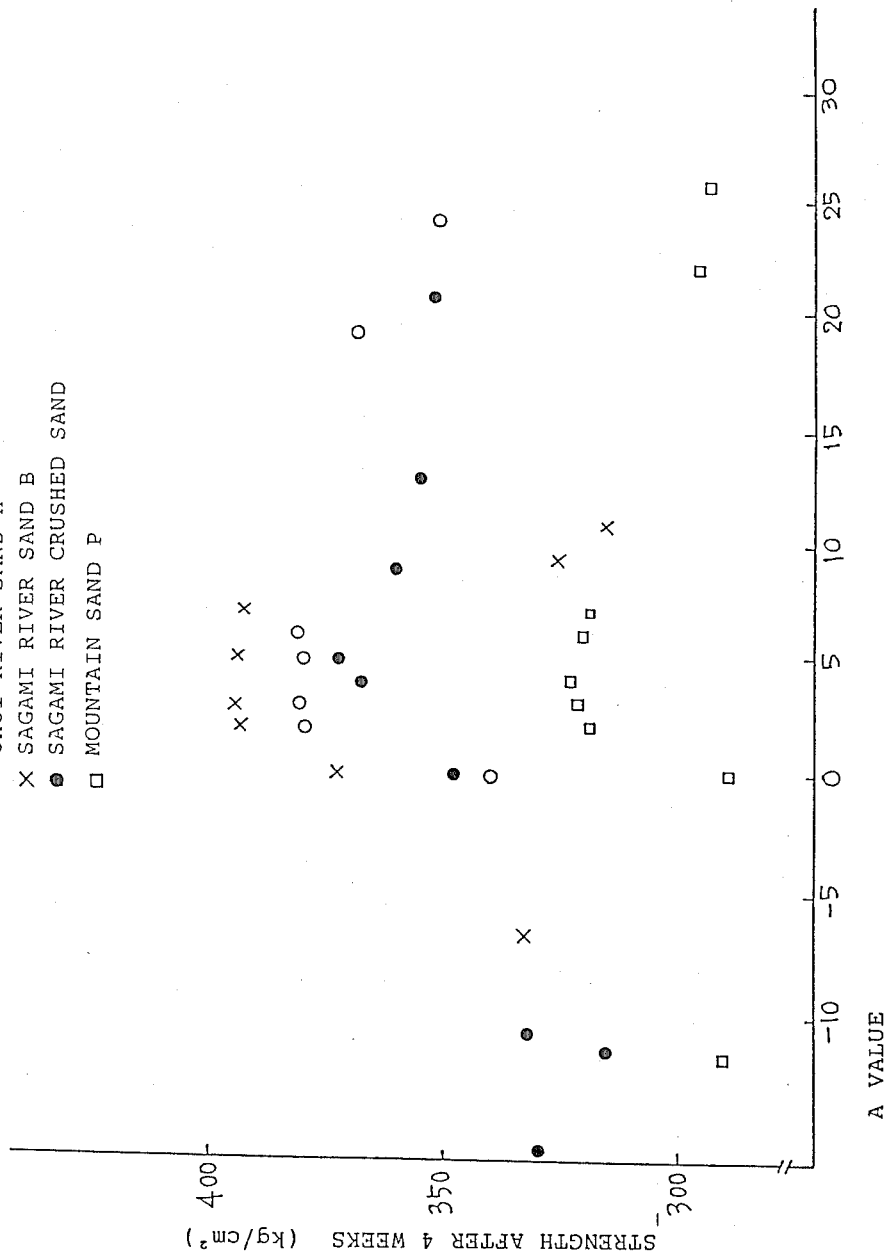
FIG. 16 is a graph showing relationship between 4-weeks strength of mortars prepared in the same manner as in the case of FIGS. 12 and 14 and a multiple of $\beta$lim.

The 4-weeks compression strength of the resulting mortars prepared according to the method of the invention and having S/C=2 was measured and shown in FIG. 16. As shown, mortars which were prepared by incorporating the primary water in a quantity determined based upon the multiple A of about 4, in general of 2–7, will manifest high compression strength. More particularly, when selecting the multiple A to be within the above range, the compression strength of mortars were increased by more than 50 kg/cm² for the Sagami River sand B, by more than 20 kg/cm² for the Ohio River sand F, by more than 10 kg/cm² for the Sagami River crushed sand and by more than 25 kg/cm² for the mountain sand P, and the highest strength could be obtained in the case of A being in a range of 3–6.

EXAMPLE 2

A river sand collected in Yuhutsu, Hokkaido, having a particle diameter of less than 5 mm and a sand prepared by minutely crushing a stone were used together with a fine gravel to prepare a concrete mixture. More particularly, 1248 kg/m³ of the Yuhutsu River sand having Q=1.94% and $Q_0$=0.78% and 64 kg/m³ of the minutely crushed sand having Q=3.37% and $Q_0$=1.8% were mixed together to obtain a sand mixture having Q=2.01% and $Q_0$=0.83%, and to the sand mixture is added 718 kg/m³ of the fine gravel and 450 kg/m³ of an ordinary Portland cement (in this case the ratio S/C=(1248+64)/450=2.92) and the primary and secondary water to thereby prepare a concrete having a water to cement ratio of 30.9% (measured based on the absolutely-dry condition). In the equation of $W_1/C = W_p/C + \beta_0 S/C$ which is referred to hereinbefore, the ratio $W_p/C$ was made to be 17%, and $\beta_0 = 1.18 \times 2 = 2.36\%$ as $\beta \lim = Q - Q_0 = 2.01 - 0.83 = 1.18\%$ and the multiple A was made to be 2, so that:

$W_1/C = 17 + 2.36 \times 2.92 = 23.9\%$.

A quantity of the primary water was determined by the ratio $W_1/C$ thus determined and the secondary water had the remaining portion of water quantity necessary to prepare the concrete.

A surface-dry specific gravity of the fresh concrete thus prepared was 2.45 kg/l and a filling-up coefficient of a compact body made of the fresh concrete was 95.4% which is very high irrespective of its lower W/C ratio of 30.9%. On the contrary, another fresh concrete prepared based on the prior art concept had a filling-up coefficient of 92.3%, proving the fact that the filling-up coefficient can be remarkably improved by the method of the invention. Moreover, the compact body made of the fresh concrete prepared by the method of the invention had a compression strength of 409 kg/cm² which is considerably high, and the result of the water permeability test revealed 3 mm decrement of water level after two hours which should be compared with 150 mm decrement of a control compact body prepared by the prior art method.

EXAMPLE 3

Concrete mixtures were prepared by different series of kneading steps, as follows, by using an ordinary Portland cement (C), a hill sand (S) collected in Nishi-oketa, Kagawa-ken having FM=2.7, a stone-crushed gravel (G) collected in Naruto, Tokushima-ken and an additive (Ad) called "VINSOL" (Trade Mark) made by Yamasoh Kagaku K.K., respectively. In the following diagrammatic equations, $W_1$ and $W_2$ mean primary and secondary water, and a symbol→a kneading step, respectively.

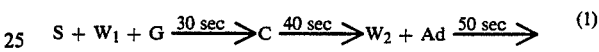
(1)

(2)

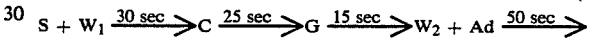
(3)

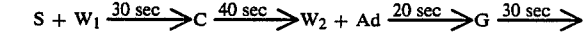
(4)

(5)

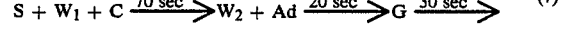
(6)

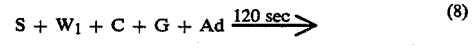
(7)

$$S + W_1 + C + G + Ad \xrightarrow{120 \text{ sec}} \quad (8)$$

The sand (S) used in the respective kneading steps had water absorption of 2.05%, surface-dry specific gravity of 2.51 kg/l, Q of 2.05%, $Q_0$ of 0.73% and $\beta$lim of 1.32, the last three values having been determined by the centrifugal froce applying treatment of the invention. In each of the kneading steps (1)–(7), the ratio $W_1/C$ was determined on the assumption that A=3. Thus, $\beta \max = A \times \beta \lim = 3 \times 1.32 = 3.96$ (%)

$\beta_0 = \beta \max + Q_0 = 3.96 + 0.73 = 4.69$ (%)

so that the ratio $W_1/C$ in the absolutely-dry condition can be determined by the following equation wherein the ratio $W/C_p$ was predetermined to be 24% which is represented by $\alpha$:

$W_1/C = \alpha + \beta_0 + S/C = 24 + 4.69 \times 3.32 = 39.6$ (%)

while the ratio $W_1/C$ in the surface-dry condition can be determined by:

$W_1/C = \text{absolutely-dry } W_1/C - Q \times S/C$

-continued
= 39.6 − 2.05 × 3.32 = 32.8 (%)

The total kneading period in the respective steps (1)–(8) were made equal, that is 120 seconds. The compositions of the resulting concrete mixtures per meter cube are shown in the following Table III.

TABLE III

| W/C (%) | S/a (%) | S/C | C (kg) | S (kg) | G (kg) 2005 | G (kg) 4020 | W (kg) | Ad (kg) |
|---|---|---|---|---|---|---|---|---|
| 64.8 | 44.6 | 3.32 | 251 | 834 | 1064 690 | 374 | 162.6 | 0.15 |

In this table the ratio W/C is shown as that determined in the surface-dry condition, which will correspond to the absolutely-dry W/C of 71.6%.

Fresh concrete mixtures prepared by the respective kneading steps (1)–(8) had characteristics shown in the following Table IV.

TABLE IV

| kneading method No. | $W_1/C$ (%) | slump (cm) | air content (%) | kneading finish temp. (°C.) | bleeding (%) | strength (kg/cm²) | average strength (kg/cm²) | standard deviation (kg/cm²) | variation coefficient (%) |
|---|---|---|---|---|---|---|---|---|---|
| 1 | | 6.1 | 3.8 | 22 | 1.06 | 260,256,257 | 258 | 1.7 | 0.7 |
| 2 | | 6.5 | 3.1 | 22.5 | 1.43 | 243,250,246 | 246 | 2.9 | 1.2 |
| 3 | | 7.1 | 3.5 | 21.5 | 1.37 | 245,241,249 | 245 | 3.3 | 1.3 |
| 4 | 32.8 | 6.1 | 3.2 | 23 | 1.51 | 242,233,235 | 237 | 3.9 | 1.6 |
| 5 | | 8.0 | 4.1 | 23.5 | 1.96 | 235,240,249 | 241 | 5.8 | 2.4 |
| 6 | | 6.9 | 3.9 | 22 | 1.62 | 245,235,239 | 240 | 4.1 | 1.7 |
| 7 | | 7.3 | 3.7 | 22 | 2.23 | 233,230,244 | 236 | 6.0 | 2.6 |
| 8 | — | 8.3 | 4.2 | 20.5 | 4.92 | 219,198,208 | 208 | 8.6 | 4.1 |

As shown in this table, it is understood that the fresh concrete mixtures prepared by the method of this invention are substantially free from bleeding and have high compression strength after 4 weeks with lesser standard deviation and variation coefficient, meaning that a concrete mixture having improved characteristics can be constantly obtained.

EXAMPLE 4

In this example fresh concrete mixtures were prepared by using an ordinary Portland cement (C), a sand mixture of the Ashida River sand ($S_1$) in Hiroshima-ken having FM=2.96 and the sea sand ($S_2$) in Kagawa-ken having FM=2.60, a stone-crushed gravel (G) in Araya, Hiroshima-ken having FM=6.53 and an additive (Ad) comprising POZOLIS No.8 (Trade Mark), with the multiple value A being varied.

The composition of the resulting concrete mixtures per meter cube are shown in the following Table V in which W/C is shown as that determined in the surface-dry condition which will be equivalent to the absolutely-dry W/C ratio of 65.4%.

TABLE V

| W/C (%) | S/a (%) | cement (kg) | sand $S_1$ (kg) | sand $S_2$ (kg) | crushed stone (kg) | water (kg) | additive (kg) |
|---|---|---|---|---|---|---|---|
| 61 | 51.7 | 343 | 428 | 428 | 860 | 209 | 0.86 |

The results of the centrifugal force applying test regarding the respective sand ($S_1$) and ($S_2$) and a mixture thereof are shown in the following Table VI.

TABLE VI

| mix ratio | | Q (%) | $Q_0$ (%) | lim (%) |
|---|---|---|---|---|
| $S_1$ | 1 | 1.70 | 0.46 | 1.24 |
| $S_2$ | 1 | 1.91 | 0.33 | 1.58 |
| mixture | | 1.805 | 0.395 | 1.41 |

The concrete mixtures were prepared according to the kneading methods (1) and (8) referred to in Example 3, respectively. In the method (1), the ratio $W_1/C$ was determined by the multiple value A varying from 0 to 7. The values $\beta$max, $\beta_0$, absolutely-dry $W_1/C$ and surface-dry $W_1/C$ are shown in the following Table VII wherein $\alpha = W/Cp = 24\%$.

TABLE VI

| A | $\beta$max (A × $\beta$lim) | 0 ($\beta$max + $Q_0$) | absolutely-dry $W_1/C$ ($W_1/C = \alpha + \beta_0 \times S/C$) | surface-dry $W_1/C$ (absolutely-dry $W_1/C$ − Q × S/C) |
|---|---|---|---|---|
| 0 | 0 | 0.395 | 25.0 | 20.5 |
| 3 | 4.23 | 4.625 | 35.6 | 31.1 |
| 5 | 7.05 | 7.445 | 42.6 | 38.1 |
| 7 | 9.87 | 10.265 | 49.7 | 45.2 |

Characteristics of the respective fresh concrete mixtures thus prepared were measured and are shown in the following Table VIII.

TABLE VIII

| A | $W_1/C$ (%) | slump (cm) | air content (%) | bleeding (%) | strength (kg/cm²) | average strength (kg/cm²) | standard deviation (kg/cm²) | variation coefficient (%) |
|---|---|---|---|---|---|---|---|---|
| 0 | 20.5 | 19.6 | 4.4 | 6.6 | 256,249,250 | 252 | 3.1 | 1.2 |
| 3 | 31.1 | 18.8 | 4.5 | 3.3 | 266,269,262 | 265 | 2.9 | 1.1 |
| 5 | 38.1 | 18.9 | 4.4 | 3.8 | 258,262,264 | 261 | 2.5 | 1.0 |
| 7 | 45.2 | 18.7 | 4.9 | 4.5 | 260,255,261 | 259 | 2.6 | 1.0 |
| — | — | 19.6 | 4.6 | 7.5 | 223,230,241 | 231 | 7.4 | 3.1 |

As shown, when selecting the multiple value A to be 3–7, the fresh concrete mixtures having improved strength could be obtained with lesser standard deviation and variation coefficient.

EXAMPLE 5

In this example, in place of the Q value determined by the method prescribed in JIS A1109, another value $Q'$ which will be equivalent thereto was determined by the presser reducing treatment followed by the centrifugal force applying treatment. A sand mixture was used by mixing 1:1 of a coarse particle sand (FM=3.62) and a fine particle sand (FM=1.73), both collected in Hannoh, Saitama-ken.

The sand mixture thus prepared was made to be in an absolutely-dry condition, 12% water was added thereto and $Q'$ was determined by the following two methods:

$$-730 \text{ mmHg} \xrightarrow{2.5 \text{ min. mix.}} \text{atmosphere} \cdot \quad (A)$$

$$-730 \text{ mmHg} \xrightarrow{2.5 \text{ min. mix.}}$$

$$\text{atmosphere} \xrightarrow{5 \text{ min. mix.}} \quad (B)$$

Respective sand which had been treated as (A) and (B) were subjected to an equalization treatment (for example, with a centrifugal force of 4.53 g for 3 minutes), and then subjected to the centrifugal force applying treatment according to the invention for 30 minutes so as to determine the value $\beta z$. Thus, the value $\beta z$ in the case of (A), which is hereby defined by $\beta z'$, was 5.38 and the value $\beta z$ in the case of (B), which is shown by $\beta z''$, was 4.92. $Q_0'$ could be obtained by subtracting $\beta z''$ from $\beta z'$, that is (5.38−4.92= 0.46), and $Q'$ which will be equivalent to Q could be obtained by:

$$\frac{Q_0'(A'+1)+\beta z'}{A'} = \frac{0.46(2.86-1)+5.38}{2.86} = 2.18$$

It was confirmed that similar good results were obtained by utilizing the values $Q'$ and $Q_0'$ and by selecting the multiple A to be 3–5.

EXAMPLE 6

Various sand samples having characteristics (measured by JIS methods) shown in the following Table I were prepared. One of each sample was dried up at a temperature of 110° C. for 24 hours and then subjected to water absorption treatment in a pressure condition of −730 mmHg for 5 minutes so as to have water content of three times of the Q value shown in Table IX, whereas the other was treated as in a surface-dry condition prescribed in JIS A1109.

TABLE IX

| sample | FM | Q (%) | ε (%) | surface-dry specific gravity | absolutely-dry specific gravity |
|---|---|---|---|---|---|
| granulated slag sand A | 2.54 | 0.64 | 34.3 | 2.84 | 2.82 |
| Ohoi River F | 2.82 | 1.20 | 32.8 | 2.63 | 2.60 |
| mountain sand D | 2.51 | 1.20 | 32.1 | 2.65 | 2.62 |
| sea sand S | 2.49 | 1.91 | 37.7 | 2.59 | 2.54 |

These samples were then mixed with cement and water in a volume ratio of 2.6 to 1 cement and in the water to cement ratio W/C=68%. The mortar preparation method comprised the steps of adding the primary water to the sand followed by kneading for 30 seconds, adding the cement followed by kneading for 90 seconds and adding the secondary water followed by kneading for 60 seconds. The compositions of the resulting mixtures are shown in the following Table X.

TABLE X

| | based on absolutely-dry condition (experimental composition) | | | | | | based on surface-dry condition (JIS-Q) | | | | | | absolutely dry |
|---|---|---|---|---|---|---|---|---|---|---|---|---|---|
| | W/C | S/C | | composition (kg/m³) | | | W/C | S/C | | composition (kg/m³) | | | $W_1/C$ |
| sample | (%) | volume | weight | cement | sand | water | (%) | volume | weight | cement | sand | water | (%) |
| granulated slag sand A | 68.0 | 2.6 | 2.32 | 550 | 1276 | 374.0 | 66.0 | 2.60 | 2.34 | 555 | 1299 | 366.3 | 25.4 |
| Ohoi River F | " | " | 2.14 | 549 | 1175 | 373.3 | 65.0 | 2.60 | 2.17 | 558 | 1211 | 362.7 | 28.4 |
| mountain sand P | " | " | 2.13 | 553 | 1178 | 376.0 | 65.0 | 2.57 | 2.16 | 561 | 1212 | 364.7 | 29.5 |
| sea sand S | " | " | 2.09 | 550 | 1150 | 374.0 | 64.0 | 2.60 | 2.13 | 562 | 1197 | 359.7 | 32.0 |

Meanwhile, another test was carried out in which according to this invention, water content of about 2.5Q was considered as "non-effective" and the composition was determined as shown in the following Table I so as to obtain W/C ratio of 57%, which is substantially equivalent to W/C ratio of 68% of Table X.

TABLE XI

| | condition | | | | composition per m³ | | | | absolutely dry $W_1/C$ (%) |
|---|---|---|---|---|---|---|---|---|---|
| | W/C (%) | | S/C | | cement | absolutely dry sand | effective water (l) | | |
| sample | 2.5 Q base | absolutely dry base | volume | weight | (Kg) | (kg) | surface dry | absolute quantity | |
| granulated slag sand A | 57.0 | 60.3 | 2.6 | 2.32 | 574 | 1333 | 327.2 | 346.1 | 25.5 |
| Ohoi River F | " | 62.8 | " | 2.14 | 566 | 1211 | 322.6 | 355.4 | 29.1 |
| mountain sand P | " | 63.5 | " | 2.16 | 563 | 1216 | 320.9 | 357.5 | 29.8 |
| sea sand S | " | 66.3 | " | 2.09 | 555 | 1160 | 316.4 | 368.0 | 33.4 |

The respective mixtures shown in Table X and XI were prepared in the same conditions, namely by adding the primary and secondary water and by kneading in the same step and over the same period, as described before.

To the respective mixtures were applied the following tests for determining the characteristics or properties thereof.

(1) Bleeding on the surface—a cylindrical container having a diameter of 71 mm and a height of 200 mm was used to measure percentage of bleeding at each 1 hour interval and thus to obtain total bleeding percentage.

(2) Bleeding on the inside—a quantity of water separation was measured 90 minutes after charging.

(3) Submergence test—a submerged quantity was measured with a sinking stick having a diameter of 20 mm and in a two-liter measure, immeadiately after kneading.

(4) Table flow—measured by JIS at a constant temperature and a constant humidity, immediately after kneading.

(5) Unit weight—with a two-liter measure.

(6) Test for strength—bending and compression strength was measured on test pieces of 4×4×16 mm, after 7 and 28 days respectively.

The results of these tests are shown in Table XII for the mixtures of Table X and in Table XIII for the mixtures of Table XI.

TABLE XII

| sample | unit weight (kg/l) | table flow (cm) | submergence test (g/cm$^2$) | bleeding (%) surface Bg | bleeding (%) inside B$_F$ | strength (kg/cm$^2$) 7 days bend | 7 days comp. | 28 days bend | 28 days comp. |
|---|---|---|---|---|---|---|---|---|---|
| granulated slag sand A | 2.194 | 28.2 | 0.28 | 6.10 | 18.50 | 48.7 | 241 | 62.9 | 359 |
| Ohoi River F | 2.119 | 26.6 | 0.87 | 1.32 | 12.18 | 48.1 | 213 | 57.7 | 324 |
| mountain sand P | 2.083 | 27.9 | 0.53 | 2.36 | 13.59 | 40.6 | 194 | 53.0 | 308 |
| sea sand S | 2.062 | 25.2 | 1.81 | 1.05 | 7.80 | 51.9 | 242 | 65.1 | 366 |

TABLE XIII

| sample | unit weight (kg/l) | table flow (cm) | submergence test (g/cm$^2$) | bleeding (%) surface Bg | bleeding (%) inside B$_F$ | strength (kg/cm$^2$) 7 days bend | 7 days comp. | 28 days bend | 28 days comp. |
|---|---|---|---|---|---|---|---|---|---|
| granulated slag sand A | 2.213 | 26.3 | 1.33 | 2.97 | 12.87 | 47.8 | 266 | 68.0 | 366 |
| Ohoi River F | 2.154 | 25.1 | 2.03 | 0.71 | 8.42 | 54.7 | 243 | 69.4 | 344 |
| mountain sand P | 2.125 | 25.9 | 1.02 | 2.43 | 12.14 | 38.6 | 218 | 61.8 | 314 |
| sea sand S | 2.099 | 24.1 | 3.50 | 1.13 | 8.03 | 51.3 | 243 | 67.2 | 314 |

Comparing the results shown in Tables XII and XIII, the bleeding on the surface in Table XIII is in a range of 0.71–2.97% whereas the bleeding shown in Table XII is in a range of 1.05–6.10%, the former being much smaller and falling in a narrower range than the latter. The bleeding on the inside shown in Table XIII ranges from 8.03 to 12.87% which is also smaller than those in Table XII ranging from 7.8 to 18.5%. With regard to the submergence test, the results shown in Table XII are 0.28–1.81 g/cm$^2$ while those 10 in Table XIII are 1.02–3.5 g/cm$^2$ showing superior fluidability, and Table XIII shows less scattering results of the table flow test.

We claim:

1. A method of preparing mortar or concrete, which comprises the steps of:

determining respectively a percentage of water contained in or adhered to a fine aggregate equivalent to a JIS surface-dry water percentage, minimum and maximum adhesion water percentages of the fine aggregate, and a percentage of water of the fine aggregate in which interstice thereof is saturated with water while a surface thereof is dry;

determining a quantity of water necessary to be added for preparation of the mortar or concrete in accordance with a multiple of a given value with respect to said minimum adhesion water percentage; and mixing a powder of hydraulic compound with a fine aggregate and the calculated amount of water.

2. The method according to claim 1 wherein said multiple is selected to be 2–7.

3. A method of preparing mortar or concrete, which comprises the steps of;

determining respectively a percentage of water contained in or adhered to a fine aggregate equivalent to a JIS surface-dry water percentage, minimum and maximum adhesion water percentages of the fine aggregate, and a percentage of water of the fine aggregate in which interstice thereof is saturated with water while a surface thereof is dry;

determining a quantity of primary water to be added in accordance with a multiple of a given value with respect to said minimum adhesion water percentage; and mixing a powder of hydraulic compound with a fine aggregate and the calculated amount of primary water followed by first kneading and then adding secondary water to a resulting mixture followed by a second kneading.

4. The method according to claim 3 wherein said multiple is selected to be 2–7.

5. The method according to claim 3 wherein the quantity of said primary water is determined according to the following equation:

$$W_1/C = W_p/C + {}_0S/C$$

where
$\beta_0 = \beta\text{max} + Q_0$
$\beta\text{max} = A \cdot \beta\text{lim}$
$\beta\text{lim} = Q - Q_0$ $W_1$: water quantity existing in the primary kneading
C: quantity of powder of hydraulic compound
$W_p$: water quantity in a paste in a fanicular or capillary region
S: quantity of fine aggregate Q: water percentage equivalent to JIS surface dry water percentage
$Q_0$: water percentage of fine aggregate in which interstice is saturated with water while a surface is dry
$\beta_0$: water percentage of fine aggregate on which surface water is deposited to the maximum
$\beta$max: maximum adhesion water percentage of fine aggregate
$\beta$lim: minimum adhesion water percentage of fine aggregate
A: multiple of a given value with respect to minimum adhesion water percentage of fine aggregate.

* * * * *